United States Patent [19]

Masson et al.

[11] 4,062,935

[45] Dec. 13, 1977

[54] IMMUNOASSAY INVOLVING THE BINDING OF RF TO THE ANTIGEN-ANTIBODY COMPLEX

[75] Inventors: Pierre Lucien Masson, Brussels; Joseph Felix Heremans, Leuven, both of Belgium

[73] Assignee: Technicon Instruments Corporation, Tarrytown, N.Y.

[21] Appl. No.: 578,698

[22] Filed: May 19, 1975

[30] Foreign Application Priority Data

May 20, 1974 United Kingdom .............. 22377/74

[51] Int. Cl.² .................... G01N 31/14; B01N 33/16
[52] U.S. Cl. .................... 424/12; 23/230 B; 23/230.6; 195/103.5 R; 424/8
[58] Field of Search ............. 23/230 B, 230.3, 230.6; 195/103.5 R, 103.7; 424/1, 1.5, 12

[56] References Cited

U.S. PATENT DOCUMENTS

| 3,654,090 | 4/1972 | Schuurs et al. ............... 195/103.5 R |
| 3,658,982 | 4/1972 | Reiss et al. ............................ 424/12 |
| 3,852,157 | 12/1974 | Rubenstein et al. ............... 424/12 X |
| 3,992,517 | 11/1976 | Lowke .................................... 424/12 |

OTHER PUBLICATIONS

*Gradwohl's Clinical Laboratory Methods and Diagnosis,* 7th ed., vol. 2, Mosby Co., St. Louis, pp. 1471–1474, 1561–1562, 1566–1571, (1972).

*Chem. Abstr.,* vol. 81, 36322t, (1974).

Cowdery, Jr. et al., *J. Immunol.,* vol. 114, pp. 5–9, (1975).

Nydegger et al., *J. Clin. Invest., vol.* 54, pp. 297–309, (1974).

*Primary Examiner*—Sidney Marantz
*Attorney, Agent, or Firm*—S. P. Tedesco

[57] ABSTRACT

A method for analyzing a biological fluid sample for Ab, Ag, or Ab:Ag complexes therein which includes the step of adding to the sample a solution of RF or Clq to bind with Ab:Ag complexes present or formed therein, and thereafter analyzing the mixture so formed for complexes bound to RF.

31 Claims, No Drawings

IMMUNOASSAY INVOLVING THE BINDING OF RF TO THE ANTIGEN-ANTIBODY COMPLEX

This invention is concerned with the analysis of biological fluids, such as urine or serum, for the determination of the presence, amount and/or nature of antibodies, antigens and antibody:antigen complexes. (For simplicity hereinafter the symbols "Ab," "Ag" and "Ab:Ag" are used for "antibody," "antigen," and "antibody-antigen complex," respectively.)

As is well known, it is important to be able to analyse biological fluids for Ab, Ag and Ab:Ag complexes. For example many diseases are characterised by the presence in the circulation of Ab:Ag complexes. The Ag may be any of a wide variety of proteins including those due to the presence of bacteria or viruses or those released from human tissues or cancer cells. The Ab are, of course, specific to the particular Ag and are predominantly immunoglobulins of the IgG class synthesised by the subject's lymphoid system. The detection of Ab:Ag complexes in blood, and their separation and characterisation, provide information of value and can be used, for example, in the diagnosis of disease.

There are a number of techniques known for detecting and quantifying Ag, Ab and Ab:Ag complexes and particularly for determining the nature and amount of Ag present. These quantification techniques are called "immunoassay" procedures.

It has been known for some time that two naturally occurring substances, namely rheumatoid factor (RF) and a particular component of complement, namely C1q, have the property of combining with Ab:Ag complexes but not with either free Ag or free Ab. Whilst there has been a prior proposal (Agnello et al., J. Exp. Med., 134, 228, 1971) to use this property in one particular way for the detection (but not the quantitative assay or absolute determination) of Ab:Ag complexes, it has never previously been realized that RF and C1q are potentially extremely useful reagents in the analysis of Ab, Ag and Ab:Ag complexes.

We have now found that solutions of RF and C1q are in fact very widely applicable reagents in analytical procedures involving Ab, Ag and/or Ab:Ag complexes and their use can, for example, simplify and render more accurate immunoassay techniques.

RF is a known material and methods for its preparation and isolation are known. It is present, or can be made to appear, in the blood of a number of animal species including man. It is normally obtained from goats or rabbits by intradermal injections of their own purified immunoglobulins previously aggregated by heating at about 63° C for about 10 minutes. RF is then isolated from the serum obtained from the animals, by passing the serum through a column of aggregated immunoglobulins on which it is retained. The RF can then be eluted from the column using as eluant a solution of the appropriate pH or salt concentration.

C1q is a natural circulating protein and method for its separation and purification are known. It is usually obtained from human, rabbit or bovine serum by a technique known as "euglobulin precipitation" which is described in, for example, J. Immunol., 106, 304-413 (1971).

In its broadest aspect, the invention provides a method of analysing a biological fluid sample for Ab, Ag or Ab:Ag complexes therein which includes the step of adding to the sample, before or after adding other reagents, a solution of RF or C1q to bind with Ab:Ag complexes present therein.

There is a large number of ways of carrying out this method, including the following preferred procedures:

i. A method of assaying an Ab or Ag in a biological fluid sample, which comprises the steps of:
 a. adding to the sample an excess of an Ag or Ab which is specific to the Ab or Ag, respectively, in the sample to form an Ab:Ag complex;
 b. adding to the mixture formed in step (a) a known amount of a solution of RF or C1q in excess of that required to bind with all the said Ab:Ag complex present, the RF/Ab:Ag or C1q/Ab:Ag formed agglomerating in the mixture;
 c. separating from the mixture the agglomerated RF/Ab:Ag or C1q/Ab:Ag, and
 d. measuring the amount of RF or C1q remaining in the mixture after step (c) or separated from the mixture in step (c), and therefrom calculating the amount of Ab or Ag present in the original sample.

Preferably, step (d) comprises
 i. adding to the mixture remaining after step (c) a known amount of a complex Ab':Ag' in excess of the amount required to bind with all the RF and C1q in the mixture, the complex Ab':Ag' carrying an identifying label; and
 ii. measuring the amount of Ab':Ag' which remains free in the mixture unbound to RF or C1q. Preferably, in this procedure, the identifying label is an enzyme or co-enzyme such that the activity of the enzyme or coenzyme is inhibited upon binding of the Ab':Ag' complex to RF or C1q, and the amount of free Ab':Ag' is determined by measuring the enzyme or coenzyme activity of the mixture without first remaining the RF/Ab':Ag' or C1q/Ab'λ:Ag.

ii. A method of assaying an Ab:Ag complex in a biological fluid sample, which comprises the steps of:
 a. adding to the sample a known amount of a solution of RF or C1q in excess of the amount required to bind with all the Ab:Ag complex in the sample to form RF/Ab:Ag or C1q/Ab:Ag, the said RF/AB:Ag or C1q/Ab:Ag agglomerating in the mixture;
 b. separating from the mixture the agglomerated RF/Ab:Ag or C1q/Ab:Ag; and
 c. measuring the amount of RF or C1q remaining in the mixture after step(b) or separated from the mixture in step (b), and therefrom calculating the amount of Ab:Ag complex present in the original sample.

iii. A method of assaying an Ab or Ag in a biological fluid sample, which comprises the steps of:
 a. adding to the sample an excess of an Ag' or Ab' which is specific to the Ab or Ag, respectively, in the sample, to form an Ab:Ag' complex or Ab':Ag complex, the Ab' or Ag' carrying an identifying label;
 b. adding to the mixture formed in step (a) a solution of RF or C1q in an amount at least sufficient to bind with all the Ab:Ag' or Ab':Ag complex in the mixture; and
 c. measuring the amount of Ab' or Ag' free in the mixture or bound to the RF or C1q, and therefrom calculating the amount of Ab or Ag present in the original sample.

iv. A method of assaying an Ab:Ag complex in a biological sample which comprises the steps of:
 a. adding to the sample a known amount of an Ab':Ag complex which carries an identifying label, and a solution of RF or C1q in an amount insufficient to bind with the total amount of Ab:Ag and Ab':Ag' complexes in the mixture formed, and b. measuring the amount of Ab':Ag' free in the mixture or bound to the RF or C1q and therefrom calculating the amount of Ab:Ag present in the original sample.

v. A method of assaying an Ab or Ag in a biological fluid sample, which comprises a. adding to the sample an Ag or Ab which is specific to the Ab or Ag, respectively, in the sample to form an Ab:Ag complex;

b. adding to the mixture from step (a) a known amount of the Ab or Ag to be determined, which amount carries an identifying label;

c. adding to the mixture formed in step (b) a solution of RF or C1q in an amount at least sufficient to bind with all the Ab:Ag complex in the mixture; and d. measuring the amount of labelled Ab or Ag remaining free in the mixture or bound to the RF or C1q.

vi. A method of determining the presence in, or absence from, a biological fluid sample of an Ab:Ag complex, which comprises adding to the sample a solution of RF or C1q and a material which is caused to agglutinate on contact with RF or C1q, and detecting whether agglutination of the material occurs.

vii. A method of detecting the presence of a particular Ab or Ag in a biological fluid sample, which comprises adding to the sample an Ag or Ab which is specific to the particular Ab or Ag whose presence is to be determined, to form with any of said particular Ab or Ag present on Ab:Ag complex; and determining the presence or absence of such complex by the method described above.

viii. A method of immunoassay of a biological fluid sample for Ab, Ag or Ab:Ag complexes, which includes the steps of (a) adding to the sample an Ab, Ag or Ab:Ag complex carrying an enzyme label;

(b) adding a solution of RF or C1q, to bind with any Ab:Ag complex present; and (c) using the inhibitory effect of RF or C1q on the enzymic activity of any labelled Ab:Ag complex bound thereto, in order to assay the sample.

The general techniques involved in carrying out these procedures will be well understood by those skilled in the art, so that detailed description thereof is unnecessary.

In the method of the invention for the assay of Ab, Ag and Ab:Ag complexes (e.g., methods (i) to (v) and (viii) above), a solution of RF or C1q is used. The RF or C1q binds with Ab:Ag complexes, but not with free Ab and free Ag. Thus, the RF and C1q effectively separate or bind up the Ab:Ag complexes, to form RF/Ag:Ab or C1q/Ag:Ab.

In certain cases, we have found that when RF/Ag:Ab or C1q/Ag:Ab are formed, they tend to agglomerate and when this happens, they can be removed such as by centrifuging or filtering, to leave a clear solution. This solution will contain either a. RF or C1q, but no Ab:Ag complexes; or b. Ab:Ag complexes but no RF or C1q, depending on whether there was used an excess or deficiency of RF and C1q. In such cases, where this efficient removal of RF/Ab:Ag or C1q/Ab:Ag is possible, quantitative assay is facilitated since it is merely necessary then to measure the amount of RF or C1q or Ab:Ag left in solution or removed from solution. (The RF/Ag:Ab and C1q/Ag:Ab removed can be treated with buffers to release the Ab:Ag from the RF or C1q.)

This can be most conveniently achieved using materials which carry an identifying label, such as a radioactive atom, or an enzyme or co-enzyme, or a fluorescent group. The use of such labels is well known for Ab, Ag and Ab:Ag complexes, although is has never previously been proposed to label RF or C1q. Accordingly, in another aspect, the invention includes a solution of RF or C1q, which RF or C1q carries an identifying label.

Where an Ab:Ag complex carries (on either the Ab or the Ag) an enzyme label, which enzyme has a substrate of very large molecular weight, such as amylase whose substrate is starch, we have found that when the complex binds to RF or C1q, the activity of the enzyme is inhibited. Such an enzyme lable may be bound to either the Ab or the Ag by he technique of Miles and Hales, *Nature,* 219, 186 (1968). When such inhibition occurs, it is no longer necessary in assay procedures to remove the RF/Ab:Ag or C1q/Ab:Ag from the test mixture since the overall enzymic activity of the mixture will be due only to labelled Ab or Ag which is not bound to RF or C1q. This is a very advantageous feature of the use of RF and C1q, in immunoassays involving enzymic labelling. Hitherto, it has been necessary to remove the Ab:Ag complex from the test mixture before determining the enzymic activity. When RF and C1q are used, with a suitable enzymically-labelled Ab or Ag system, removal of the Ab:Ag complex is unnecessary. This simplification in procedure greatly facilitates continuous flow analysis procedures.

Solutions of RF and C1q are useful in all types of immunoassays. For example, they can be used in assays of an Ab or Ag, in which the whole of the Ab or Ag is converted to a complex Ab:Ag, or they can be used in competitive binding assays. Among the latter are processes in which insufficient RF or C1q is added to a test mixture, to bind all the Ab:Ag complex and labelled Ab:Ag complex therein. The amount of labelled complex which becomes bound to the RF or C1q, or remains unbound, is then determined from which the amount of Ab, Ag or Ab:Ag in the original test sample can be determined. In another type of competitive binding assay, competition occurs between a labelled and an unlabelled Ag (for example) for a limited amount of Ab, the RF and C1q being used to bind the complex so formed and effectively separate it from the unbound Ag.

Solutions of RF and C1q are particularly useful in continuous flow analysis of biological fluid samples, and the invention includes such use.

Some of the procedures described above are now further described in more detail, by way of illustration only.

COMPETITIVE BINDING ASSAY

This involves competition between two Ab:Ag complexes for a limited amount of RF or C1q. Thus, for example, if an excess of a labelled Ab:Ag complex is added to a limited amount of RF or C1q, then all the RF or C1q will become bound to the complex. If, then, in addition to the labelled complex, a serum sample is added containing unlabelled Ab:Ag complex, the labelled and unlabelled complex will compete on molar terms for the limited amount of RF or C1q. If, after equilibrium is reached, the RF or C1q is removed together with the complexes bound thereto, the presence (or the presence of a particular minimum amount) of labelled complex in the remaining solution indicates that the serum sample contained an Ab:Ag complex.

This method can be operated quantitatively to measure the amount of complex in the serum sample, and it may be used for detecting the presence of a particular Ag or Ab, by establishing the presence or otherwise of an Ab:Ag complex after adding the specific Ag or Ab.

In the above procedure, the Ab:Ag bound to the RF or C1q may be removed if its insoluble or otherwise selectively removable from the solution. On the other hand, where for example, enzymic labelling is involved and there is inhibition of enzymic activity on binding to RF or C1q, the bound Ab:Ag need not be removed.

DETECTION AND ASSAY OF ANTIGEN

An antigen, such as morphine, can be detected and assayed as follows. Morphine is labelled with an enzyme, e.g., amylase. Specific anti-morphine antibodies, Ab" are prepared. The sample of serum or urine, for example, to be tested for morphine, is mixed with the Ab". Any morphine present will form a complex with the Ab". There is then added the enzyme-labelled morphine. This will only be able to complex with the Ab" in proportion to the concentration of morphine in the serum or urine. A solution of RF or C1q is then added.

The RF or C1q binds with the complexes formed between Ab" and the morphine (if any) in the serum and the labelled morphine, and forms agglomerates. As a result, the Ab": labelled morphine complexes so bound lose their enzymatic activity and it is then simply necessary to measure the enzymatic activity of free labelled morphine in the solution. If desired, the agglomerated RF/Ab": morphine complexes can be removed from the solution although this is not essential. A similar procedure may be used for other antigens and, mutatis mutandis for antibodies.

This procedures illustrate a very useful feature of the use of solutions of RF and C1q, namely that when they bind to Ab:Ag complexes in which the Ab or Ag is labelled with certain enzymes, agglomeration occurs with the result that the activity of the enzyme is inhibited.

GENERAL IMMUNOASSAY PROCEDURE

It is often desirable to be able to measure the amount of an Ab, Ag or Ab:Ag complex present in a sample liquid, and there are known techniques (immunoassay procedures) which enable this to be done. We have found that RF and C1q can be used in immunoassay procedures to advantage either in simplifying the overall procedure or in ensuring greater certainty and accuracy in the results.

We give below one general example of the use of a solution of RF or C1q in an immunoassay procedure, but it must be understood that RF and C1q can with advantage be used in other immunoassay procedures, as will be clear to those skilled in the art.

By way of example, in a typical known radiometric immunoassay procedure for assaying an antigen Ag, there is added to the solution of Ag, a known amount of the same Ag but which is radioactively labelled, Ag*. There is also added a known amount of the specific antibody for Ag (and Ag*) namely Ab. Complexes are formed, Ab:Ag and Ab:Ag* and these are separated out leaving a liquid containing Ag and Ag*. The amount of Ag* either in the separated complexes or in the liquid can be measured, and the amount of Ag originally in the sample can then be calculated.

Whilst this known procedure is effective, it is laborious to carry out since, for every particular Ag (or Ab) to be measured, the radioactive labelled Ag* (or Ab*) must be obtained.

By using a solution of RF or C1q, this disadvantage can be overcome. For example, there is first added to the sample (containing the Ag to be determined), an excess of its specific antibody Ab. A complex, Ab:Ag, is formed. There is then added a known amount of a solution of RF or C1q, in excess of the amount required to bind with all the Ab:Ag complex. The RF/Ab:Ag formed agglutinates and can be removed, thus leaving in solution the excess RF or C1q (i.e., the original amount added less the amount which bound to the Ab:Ag complex). This remaining excess can then be measured, so allowing one to calculate the amount of Ag originally in the sample.

The excess RF (or C1q) may be measured, for example, by using labelled RF or C1q, or by adding to it a known and excess amount of a labelled Ag':Ab' complex, e.g., one made from catalase (which is an antigen) and anti-catalase serum. The RF in solution binds to the labelled complex Ag': Ab' and the amount RF therein can then be calculated, ag. by measuring the enzymatic activity of the solution, optionally after removal of the complex. It may not be essential to remove the complex since whilst the enzyme catalase is large relative to the Ab and will suffer no loss of activity on forming the complex Ab:Ag, it may lose activity when the complex becomes bound to RF or C1q and agglomeration occurs.

It will be appreciated that, in the above procedure using RF or C1q, apart from the specific antibody Ab, all the reagents are standard, i.e. the RF and the labelled complex Ab':Ag'. These reagents can be used for the quantitative analysis of any Ag, or (mutatis mutandis) Ab, or complex itself, (When analysing for the complex itself, the initial step described of adding the antibody Ab, is omitted.)

CHARACTERISATION

It will be understood that many of the procedures outlined above involving the use of a solution of RF or C1q, are useful preliminaries in the characterisation of Ab, Ag or Ab:Ag complexes. Some of the procedures do directly result in identification of a particular Ab or Ag, for example, those procedures where the presence of a particular Ab is suspected and subsequently confirmed by adding the specific Ag and detecting the presence of the Ab:Ag complex.

RF and C1q are very useful reagents in the characterisation of Ab, Ag and Ab:Ag complexes, as will be clear from the foregoing description.

Identification (i.e., characterisation) of an antigen is generally effected by various procedures, e.g., spectrophotometry to detect the presence of nucleic acids, electron microscopy to identify viruses, immunofluorescence with specific antisera directed against virus or tissue antigens.

For certain purposes, it may be convenient to label RF or C1q (soluble or in their insolubilized form). This can be effected with, for example, $I^{125}$ or fluorescent or co-enzyme labelling (e.g., NADH).

Solutions of RF and C1q combine not only with Ab:Ag complexes but also with aggregated immunoglobulins. This fact should, of course, be borne in mind when carrying out the procedures described above, as will be clear to those skilled in the art. Aggregated immunoglobulins can be labelled, such as with radioactive iodine or a fluorochrome, and as such can be used in place of labelled Ab:Ag complexes in the analytical procedures described above, e.g., in the analysis procedure in place of the labelled Ab':Ag' complex.

INHIBITION OF AGGLUTINATION

RF and C1q both cause agglutination of red blood cells. Also, they will cause agglutination of materials which, for example, have a coating or outer surface of immunoglobulins, such as polystyrene particles coated with immunoglobulins. Such coatings can be formed by immunological reactions between Ab and membrane antigens, or by physical adsorption of chemical reaction. Polystyrene particles coated with immunoglobulins are commercially available but can, in any event, easily be prepared.

When such coated particles or red blood cells contact RF or C1q, agglutination begins to occur, but if there is also present in solution an Ab-Ag complex, this will react with the RF or C1q relatively quicker and the RF and C1q will become bound to the Ab:Ag complex in solution and, as a result, no agglutination of the coated particles (or red blood cells) will occur. Thus, the presence of Ab:Ag complexes in serum, for example, can be detected by contacting the serum with (soluble) RF and C1q and with particles coated with immunoglobulins. If agglutination is observed, the serum does not contain any Ab:Ag complexes.

This is a very simple and accurate test, and is applicable to the detection of all Ab:Ag complexes. An example of the procedure is as follows:

50 $\mu$l of serum are added to 50 $\mu$l of a solution of soluble C1q or RF, and the mixture is combined with 50 $\mu$l of a suspension of polystyrene particles coated with immunoglobulins. Any resulting agglutination of the particles can readily be observed.

The above test can also be used for detecting the presence of a particular Ag or Ab in serum. For example, when testing for a particular antigen, Ag', there is added to the serum the appropriate specific antibody Ab', and then the test is made for the presence of an Ab:Ag complex, namely Ab':Ag'. If the serum originally contains other Ab:Ag complexes, these must first be removed, for example using insolubilised RF or C1q as described in our copending application Ser. No. 578,699, filed May 19, 1975.

In order that the invention may be more fully understood, the following Examples are given by way of illustration only.

EXAMPLE 1

Determination of thyroxine ($T_4$)

To 100 $\mu$l of a sample containing $T_4$, there was added 100 ml of a solution containing 60 nanograms of RF and 1.00 ml of rabbit anti-human $T_4$ serum which had been appropriately diluted. The mixture was incubated overnight at room temperature, then centrifuged at 3000 g for 5 minutes, and the supernatant was removed with a Pasteur pipette and transferred to a tube containing 25 $\mu$l of aminated agarose (AH Sepharose) to which aggregated IgG had previously been covalently attached. The mixture was incubated at room temperature for 15 minutes and centrifuged to pack down the agarose particles. The supernatant was removed, the residue was shaken with 1 ml of 0.5N aqueous ammonium thiocyanate solution, and the supernatant was then quantitatively analysed for IgM by a conventional method.

The concentration of $T_4$ was inversely proportional to the final concentration IgM or RF remaining.

EXAMPLE 2

Determination of IgE 0.1 ml of the sample to be tested was pipetted into a 5 ml centrifuge tube and 1.0 ml of rabbit anti-human IgE antiserum (diluted 1:128) and 0.1 ml of commercially available $I^{125}$IgE (60,000 cpm) were added. The mixture was incubated at 37° C for 1 hour and 0.1 ml. of an RF solution containing 100 nanograms of RF was then added. Incubation was continued for another hour and the mixture was then centrifuged at 2000 rpm for 5 minutes. The supernatant was removfed and the radioactivity was measured with a gamma counter. The concentration of IgE was inversely dependent on the radioactivity count and could be determined from a previously established calibration curve.

EXAMPLE 3

Determination of IgE 0.1 ml of the sample containing IgE was pipetted into a 5 ml tube and 1.0 ml of rabbit anti-human IgE antiserum (diluted 1:128) was added. The mixture was incubated for 1 hour at 37° C and 1 ml of a solution containing 60,000 latex particles of 0.8 micron diameter which had previously been incubated in a solution of physiological saline containing 1 mg of IgG/ml., was added. The mixture was shaken and 0.1 ml of a solution containing 600 nanograms of RF (or C1q) was added.

The mixture was incubated overnight and then counted in a particle counter capable of rejecting particles greater than 1 micron in diameter. The concentration of IgE was inversely proportional to the particle count and could be determined from a previously prepared calibration curve obtained with solutions containing known concentrations of IgE.

EXAMPLE 4

Automatic analysis for $\alpha_1$ foetal protein

A flow of 0.1 ml/minute of the sample to be tested was pumped into an automatic analyser of the continuous flow type, together with the same flow of a solution containing 60,000 particles of latex per ml. The latex particles were 0.8 micron in diameter and the solution had previously been incubated with an antiserum to $\alpha_1$ foetal protein diluted 1:64 with physiological saline. The mixed streams were segmented with air pumped into the system at 0.32 ml/minute. Following the introduction of the air, a flow of 0.4 ml/minute of a solution of C1q was introduced.

The segmented stream was heated to 37° C for 10 minutes and then further heated to 63° C for 2 minutes to destroy the C1q and hence release all latex particles bound by C1q, but not those bound by Ag:Ab coupling.

The stream was then passed through a particle counter which is capable of rejecting particles greater than 1 micron in diameter. The concentration of $\alpha_1$ foetal protein was inversely proportional to the particle count and could be determined from a previously prepared calibration curve obtained with solutions containing known concentrations of $\alpha_1$ foetal protein.

EXAMPLE 5

Determination of tetanus anotoxin Ag:Ab complexes

100 μl of a solution containing 400 nanograms of RF (or Clq) were added to 100 ml of serum suspected of containing tetanus anotoxin antigen. The mixture was shaken for one-half hour at room temperature and then centrifuged at 2000g for 5 minutes. The supernatant was removed and the residual RF (or Clq) was determined with aminated agarose as described above in Example 1.

EXAMPLE 6

Production of labelled RF (or Clq)

200 ml of 50 mM phosphate buffer at pH 7.4 was added to 100 μg of RF (or Clq).

The mixture was divided into 20 μl aliquots and 10 μC $I^{125}$ followed by 50 μg of Chloramine-T were added to each aliquot. Oxidation was allowed to proceed for 30 seconds and the reaction was then terminated by the addition of 50 μl of aqueous sodium metabisulphite solution, containing 50 μg of the salt.

Labelled RF (or Clq) was then separated from the $I^{125}$ by passing the above mixture down a column of Sephadex G25 and eluting the desired labelled material with the above-mentioned phosphate buffer. Eluate fractions were assayed for γ-activity and the fractions having peak activity were pooled, stoppered and frozen until required.

What we claim is:

1. A method of analyzing a biological fluid sample for Ab, Ag, or Ab:Ag complexes therein which includes the step of adding to the sample a solution of RF to bind with Ab:Ag complexes formed or present therein, and thereafter analyzing the mixture so formed for complexes bound to RF.

2. A method of assaying a particular Ab or Ag in a biological fluid sample, which comprises the steps of:
   a. adding to the sample an excess of the Ag or Ab which is specific to the particular Ab or Ag, respectively, in the sample to form the Ab:Ag complex;
   b. adding to the mixture formed in step (a) a known amount of a solution of RF in excess of that required to bind with all the said Ab:Ag complex present, the RF/Ab:Ag formed agglomerating in the mixture;
   c. separating from the mixture the agglomerated RF/Ab:Ag, and
   d. measuring the amount of RF remaining in the mixture after step (c) or separated from the mixture in step (c), and therefrom calculating the amount of particular Ab or Ag present in the original sample.

3. A method according to claim 2 wherein step (d) comprises
   i. adding to the mixture remaining after step (c) a known amount of a complex Ab':Ag' in excess of the amount required to bind with all the RF in the mixture, the complex Ab': Ag' carrying an identifying label; and
   ii. measuring the amount of Ab':Ag' which remains free in the mixture unbound to RF.

4. A method according to claim 3 wherein the identifying label is an enzyme or co-enzyme such that the activity of the enzyme or coenzyme is inhibited upon binding of the Ab':Ag' complex to RF, and the amount of free Ab':Ag' is determined by measuring the enzyme or coenzyme activity of the mixture without first remaining the RF/Ab':Ag'.

5. A method according to claim 4 wherein the AB'λ:Ag' carries, as the identifying label, catalase or amylase.

6. A method according to claim 3 wherein the RF/Ab':Ag' is removed from the mixture, and the amount of Ab':Ag' remaining in the mixture is then measured.

7. A method of assaying a biological fluid sample to detect the presence of Ab:Ag complexes therein, which comprises the steps of:
   a. adding to the sample a known amount of a solution of RF in excess of the amount required to bind with all the Ab:Ag complexes in the sample to form RF/Ab:Ag, the said RF/Ab:Ag agglomerating in the mixture;
   b. separating from the mixture the agglomerated RF/Ab:Ag; and
   c. measuring the amount of RF remaining in the mixture after step (b) or separated from the mixture in step (b), and therefrom calculating the amount of Ab:Ag complexes present in the original sample.

8. A method according to claim 7 wherein step (c) comprises
   i. adding to the mixture remaining after step (b) a known amount of a complex Ab':Ag' in excess of the amount required to bind with all the RF in the mixture, the complex Ab':Ag' carrying an identifying label; and
   ii. measuring the amount of Ab':Ag' which remains free in the mixture unbound to RF.

9. A method according to claim 8 wherein the identifying label is an enzyme or co-enzyme such that the activity of the enzyme or coenzyme is inhibited upon binding of the Ab':Ag' complex to RF, and the amount of free Ab':Ag' is determind by measuring the enzyme or co-enzyme activity of the mixture without first removing the RF/Ab':Ag'.

10. A method according to claim 9 wherein the Ab'λ:Ag' carries, as the identifying label, catalase or amylase.

11. A method according to claim 8 wherein the RF/Ab':Ag' is removed from the mixture, and the amount of Ab':Ag' remaining in the mixture is then measured.

12. A method of assaying a particular Ab or Ag in a biological fluid sample, which comprises the steps of:
   a. adding to the sample an excess of an Ag' or Ab' which is specific to particular Ab or Ag, respectively, in the sample, to form an Ab:Ag' complex or Ab':Ag complex, the Ab' or Ag' carrying an identifying label;
   b. adding to the mixture formed in step (a) a solution of RF in an amount at least sufficient to bind with all the Ab:Ag' or Ab':Ag complex in the mixture; and
   c. measuring the amount of Ab' or Ag' free in the mixture or bound to the RF, and therefrom calculating the amount of the particular Ab or Ag present in the original sample.

13. A method according to claim 12 wherein the identifying label is an enzyme or co-enzyme such that the activity of the enzyme or coenzyme is inhibited upon binding of the Ab':Ag or Ab:Ag' complex to RF, and the amount of free Ab' or Ag' is determined by measuring the enzyme or coenzyme activity of the mixture without first removing the Ab':Ag or Ab:Ag' bound to the RF.

14. A method according to claim 13 wherein the Ab' or Ag' carries, as the identifying label, catalase or amylase.

15. A method according to claim 12 wherein the Ab':Ag or Ab:Ag' bound to the RF is removed from the mixture, and the amount of Ab' or Ag' remaining in the mixture is then measured.

16. A method of assaying a biological sample to detect the presence of Ab:Ag complexes therein, which comprises the steps of:
   a. adding to the sample a known amount of an Ab':Ag complex which carries an identifying label, and a solution of RF in an amount insufficient to bind with the total amount of Ab:Ag and Ab':Ag' complexes in the mixture formed, and
   b. measuring the amount of Ab':Ag' free in the mixture or bound to the RF and therefrom calculating the amount of Ab:Ag complexes present in the original sample.

17. A method according to claim 16 wherein the identifying label is an enzyme or co-enzyme such that the activity of the enzyme or co-enzyme is inhibited upon binding of the Ab':Ag' complex to RF, and the amount of the Ab':Ag' is determined by measuring the enzyme or co-enzyme activity of the mixture without first removing the Ab':Ag or Ab:Ag' bound to the RF.

18. A method according to claim 17 wherein the Ab':Ag' carries, as the identifying label, catalase or amylase.

19. A method according to claim 16, wherein the RF/Ab':Ag' is removed from the mixture, and the amount of Ab':Ag' remaining in the mixture is then measured.

20. A method of assaying a particular Ab or Ag in a biological fluid sample, which comprises
   a. adding to the sample an Ag or Ab which is specific to the particular Ab or Ag, respectively, in the sample to form an Ab:Ag complex;
   b. adding to the mixture from step (a) a known amount of the particular Ab or Ag to be determined, which amount carries an identifying label;
   c. adding to the mixture formed in step (b) a solution of RF in an amount at least sufficient to bind with all the Ab:Ag complex in the mixture; and
   d. measuring the amount of labelled Ab or Ag remaining free in the mixture or bound to the RF.

21. A method according to claim 20 wherein the identifying label is an enzyme or co-enzyme such that the activity of the enzyme or co-enzyme is inhibited upon binding of labelled Ab or Ag complex to RF, and the amount of free labelled Ab or Ag is determined by measuring the enzyme or co-enzyme activity of the mixture without first removing the Ab:Ag bound to the RF.

22. A method according to claim 21 wherein the Ab' or Ag' carries, as the identifying label, catalase or amylase.

23. A method according to claim 20 wherein the Ab:Ag bound to RF is removed from the mixture, and the amount of labelled Ag or Ab remaining in the mixture is then measured.

24. A method according to claim 21 wherein morphine is assayed, and the labelled morphine added in step (b) carries, as its label, the enzyme amylase.

25. A method of detecting the presence in, or absence from, a biological fluid sample of Ab:Ag complexes, which comprises adding to the sample a solution of RF and a material which is caused to agglutinate on contact with RF, and detecting the degree to which agglutination of the material occurs compared with a standard mixture of said material and RF.

26. A method according to claim 25 wherein the material comprises an immunoglobulin coating on inert carrier particles.

27. A method according to claim 26 wherein the particles comprise polystyrene.

28. A method of detecting the presence of a particular Ab or Ag in a biological fluid sample, which comprises adding to the sample an Ag or Ab which is specific to the particular Ab or Ag whose presence is to be determined, to form with any of said particular Ab or Ag present an Ab:Ag complex; and determining the presence or absence of such complex by the method of claim 25.

29. A method of immunoassay of a biological fluid sample for Ab, Ag or Ab:Ag complexes, which includes the steps of
   a. adding to the sample an Ab, Ag or Ab:Ag complex carrying an enzyme label;
   b. adding a solution of RF, to bind with any Ab:Ag complex present; and
   c. using the inhibitory effect of RF on the enzymic activity of any labelled Ab:Ag complex bound thereto, in order to assay the sample.

30. A method of continuous flow analysis of biological fluid samples which includes the step of adding to the samples a solution of RF to bind with Ab:Ag complexes in or formed in the samples, and thereafter treating the mixture so formed to detect the Ab:Ag complexes bound to RF.

31. A method of detecting the presence in or absence from a biological fluid sample of Ab:Ag complexes, comprising adding to the sample a known amount of RF and a known amount of latex particles coated with IgG whereby RF becomes bound to any Ab:Ag complex present and the remainder of the RF causes agglutination of the latex particles; and determining the amount of said remainder of RF by counting the agglutinated latex particles and comparing the result with a standard curve.

* * * * *